United States Patent
Bonde et al.

(10) Patent No.: US 11,624,038 B2
(45) Date of Patent: *Apr. 11, 2023

(54) CONTINUOUS BIOMASS EXTRACTION SYSTEM AND PROCESS

(71) Applicant: Boulder Creek Technologies, LLC, Arvada, CO (US)

(72) Inventors: Steven E. Bonde, Golden, CO (US); Amara Hazlewood, Arvada, CO (US); Steve Jaasund, Federal Way, WA (US)

(73) Assignee: Boulder Creek Technologies, LLC, Arvada, CO (US)

( * ) Notice: Subject to any disclaimer, the term of this patent is extended or adjusted under 35 U.S.C. 154(b) by 158 days.

This patent is subject to a terminal disclaimer.

(21) Appl. No.: 17/176,708

(22) Filed: Feb. 16, 2021

(65) Prior Publication Data
US 2021/0162315 A1   Jun. 3, 2021

Related U.S. Application Data

(63) Continuation of application No. 17/068,017, filed on Oct. 12, 2020, now Pat. No. 10,974,164.
(Continued)

(51) Int. Cl.
*C11B 9/02* (2006.01)
*B01D 5/00* (2006.01)
(Continued)

(52) U.S. Cl.
CPC .............. *C11B 9/027* (2013.01); *B01D 5/009* (2013.01); *B01D 5/0027* (2013.01); *B01D 45/16* (2013.01);
(Continued)

(58) Field of Classification Search
CPC ...... B01D 5/006; B01D 5/0027; B01D 5/009; B01D 2259/4533; B01D 45/16;
(Continued)

(56) References Cited

U.S. PATENT DOCUMENTS 3,270,437 A    9/1966  Lara et al.
5,348,571 A *  9/1994  Weber ...................... B03C 3/06
                                                    55/524
(Continued)

FOREIGN PATENT DOCUMENTS

CN          201643760 A      11/2010
WO       2015049585 A3       4/2015
(Continued)

OTHER PUBLICATIONS

WO2017078225A1_ENG (WIPO machine translation of Rhee) (Year: 2017).*

*Primary Examiner* — Jonathan Miller
*Assistant Examiner* — Gabriel E Gitman
(74) *Attorney, Agent, or Firm* — Hall Estill Law Firm; Bryan A. Fuller

(57) ABSTRACT

A method for producing valuable organic liquid from a biomass wherein a heated gas is mixed with a biomass to produce an enriched organic vapor and a biomass waste product. The biomass waste product is separated from the enriched organic vapor. The enriched organic vapor is cooled to produce a liquid organic oil and the liquid organic oil is collected. A system for producing the liquid organic oil including a first separation unit to separate an enriched organic vapor and a biomass waste product. The enriched organic vapor and the biomass waste product are generated from mixing a heated gas and a biomass. The system also includes a wet scrubber for cooling the enriched organic vapor to generate an enriched organic smoke. The organic smoke can be transformed to the liquid organic oil in an electrostatic precipitator.

18 Claims, 3 Drawing Sheets

Related U.S. Application Data

(60) Provisional application No. 62/913,509, filed on Oct. 10, 2019.

(51) Int. Cl.
  *B01D 53/32* (2006.01)
  *B01D 45/16* (2006.01)
  *B03C 3/00* (2006.01)
  *B03C 3/41* (2006.01)
  *B03C 3/49* (2006.01)

(52) U.S. Cl.
  CPC ........ *B01D 53/323* (2013.01); *A61K 2236/00* (2013.01); *B01D 2259/4533* (2013.01); *B03C 3/00* (2013.01); *B03C 3/41* (2013.01); *B03C 3/49* (2013.01)

(58) Field of Classification Search
  CPC ................ B01D 53/323; B01D 53/002; B01D 53/1487; B01D 2252/103; B01D 2257/708; B01D 1/14; A61K 2236/00; C11B 9/027; C11B 1/10; C11B 1/104; B03C 3/00; B03C 3/41; B03C 3/49; B03C 3/06; B03C 3/017; Y02P 30/20
  See application file for complete search history.

(56) References Cited

U.S. PATENT DOCUMENTS

| | | | |
|---|---|---|---|
| 6,783,575 B2* | 8/2004 | Pasic | B03C 3/16 96/60 |
| 9,034,076 B2* | 5/2015 | Sieger | B03C 3/011 95/69 |
| 10,456,708 B2 | 10/2019 | Thomas | |
| 10,617,974 B2 † | 4/2020 | Thomas | |
| 10,974,164 B1* | 4/2021 | Bonde | B01D 5/0027 |
| 2005/0229780 A1* | 10/2005 | Spink | B01D 46/50 96/53 |
| 2010/0119606 A1 | 5/2010 | Whittle et al. | |
| 2012/0222550 A1* | 9/2012 | Ellis | B03C 3/49 95/71 |
| 2016/0325289 A1* | 11/2016 | O'Brian | B03C 3/41 |
| 2018/0078874 A1 | 3/2018 | Thomas | |
| 2019/0151771 A1* | 5/2019 | Thomas | B01D 5/0003 |
| 2019/0366231 A1 | 12/2019 | Dooley et al. | |
| 2020/0048215 A1 | 2/2020 | Thomas et al. | |
| 2020/0179471 A1 | 6/2020 | Wagner et al. | |

FOREIGN PATENT DOCUMENTS

| | | | | |
|---|---|---|---|---|
| WO | WO-2017078225 A1 * | 5/2017 | .......... | B01D 53/002 |
| WO | 2020106920 A1 | 5/2020 | | |

\* cited by examiner
† cited by third party

US 11,624,038 B2

CONTINUOUS BIOMASS EXTRACTION SYSTEM AND PROCESS

CROSS-REFERENCE TO RELATED APPLICATIONS

The present application is a continuation application of U.S. patent application having U.S. Ser. No. 17/068,017, filed Oct. 12, 2020, which is a conversion of U.S. Provisional Application having U.S. Ser. No. 62/913,509, filed Oct. 10, 2019, which claims the benefit under 35 U.S.C. 119(e). The disclosure of which is hereby expressly incorporated herein by reference.

STATEMENT REGARDING FEDERALLY SPONSORED RESEARCH OR DEVELOPMENT

Not applicable.

BACKGROUND OF THE DISCLOSURE

1. Field of the Invention

The present disclosure relates to methods and systems for extracting and condensing oils and compounds of value from a biomass, including, but not limited to hemp, herbs, and hops. More specifically, this disclosure relates to methods and systems for extracting product from plant material through hot gas vaporization and condensation via electrostatic precipitation. In one exemplary embodiment, those products are cannabinoid rich oils resulting from the hemp plant.

2. Background of Invention

These oils and other compounds are used in a wide variety of applications, including as additives in household cleansers and personal care products (e.g. shampoos, lotions, facial cleansers), flavorings, supplements, and pain relief treatments. Examples of plant matter that contains useful oils and valuable compounds include lavender flowers, hops, *eucalyptus* leaves, peppermint leaves, tea tree leaves, jojoba seeds, rose petals, *cannabis* flowers, and jasmine flowers. Processes for extracting oils and compounds of value from biomass commonly employ a solvent, such as ethyl alcohol (ethanol), which is highly flammable and facilities are limited in quantities they can store, or supercritical carbon dioxide ($CO_2$), which must be operated at pressures significantly above atmospheric pressure. In addition, the extract produced from these kinds of processes often undergo further post-extraction processes that use harmful or flammable solvents to refine or isolate these compounds.

In addition to extracting desirable plant constituents, commonly employed solvent-based extraction processes may also remove undesirable ballast from the plant material. Ballast may include certain plant constituents such as fats, waxes, carbohydrates, proteins, and sugars. This ballast may alter odor, taste, consistency and/or color of the extract. It may also limit shelf life of the resulting extracts, often resulting in the need for additional processing steps to remove certain forms of ballast from that extract. The current processes for extracting oils and/or compounds of value from biomass can be time-intensive, labor intensive, resource intensive, and/or require multiple pieces of specialized equipment to yield an acceptable product. In addition, these processes only produce limited-size batches of a product rather than a continuous output.

Accordingly, there is a need for a new method and system for efficiently extracting desirable constituents from plant material. More specifically, there is a need for a new extraction method that requires less time, labor, resources, and/or specialized and energy inefficient equipment than existing methods. There is also a need for scalable extraction and condensation methods and apparatus that produces a continuous output of product without requiring a large volume of potentially flammable or hazardous solvent.

SUMMARY OF THE DISCLOSURE

The present disclosure is related to a method for producing valuable organic liquid from a biomass. A gas is heated to a predetermined temperature to produce a heated gas. The heated gas is mixed with a biomass to produce an enriched organic vapor and a biomass waste product. The biomass waste product is separated from the enriched organic vapor. The enriched organic vapor is cooled to produce a liquid organic oil and the liquid organic oil is collected.

The present disclosure is also directed to a system for producing the liquid organic oil. The system includes a heat source for heating a gas to produce a heated gas and a first separation unit to separate an enriched organic vapor and a biomass waste product. The enriched organic vapor and the biomass waste product are generated from mixing the heated gas and a biomass. The system also includes a wet scrubber for cooling the enriched organic vapor to remove certain compounds from the enriched organic vapor to generate an enriched organic smoke. The organic smoke can be transformed to the liquid organic oil in an electrostatic precipitator.

DETAILED DESCRIPTION OF THE DISCLOSURE

A continuous process for extracting oils and/or compounds of value from plant material includes passing the plant material into a heated air or gas stream for a predetermined duration within a predetermined temperature range sufficient to vaporize the essential oils and/or compounds of value of the plant material without causing pyrolysis of the plant material. The vaporized oils and/or compounds of value may be swept from the plant material by a flow of gas and then condensed to liquid form using a unique electrostatic precipitation condenser. The resulting liquid may then be distilled to isolate certain desirable compounds as preferred. The method described herein may enable useful separation of certain desirable plant constituents, which are not volatile at ambient temperatures, to be extracted upon exposure to a predetermined temperature for a predetermined duration. The method allows for extraction of oils and botanical compounds without requiring a solvent and without operating the system at pressures significantly above atmospheric pressure. The system disclosed herein can continuously be fed the plant material and continuously produce oils and botanical compounds and does not require the production to be performed in batches.

Figure 1:
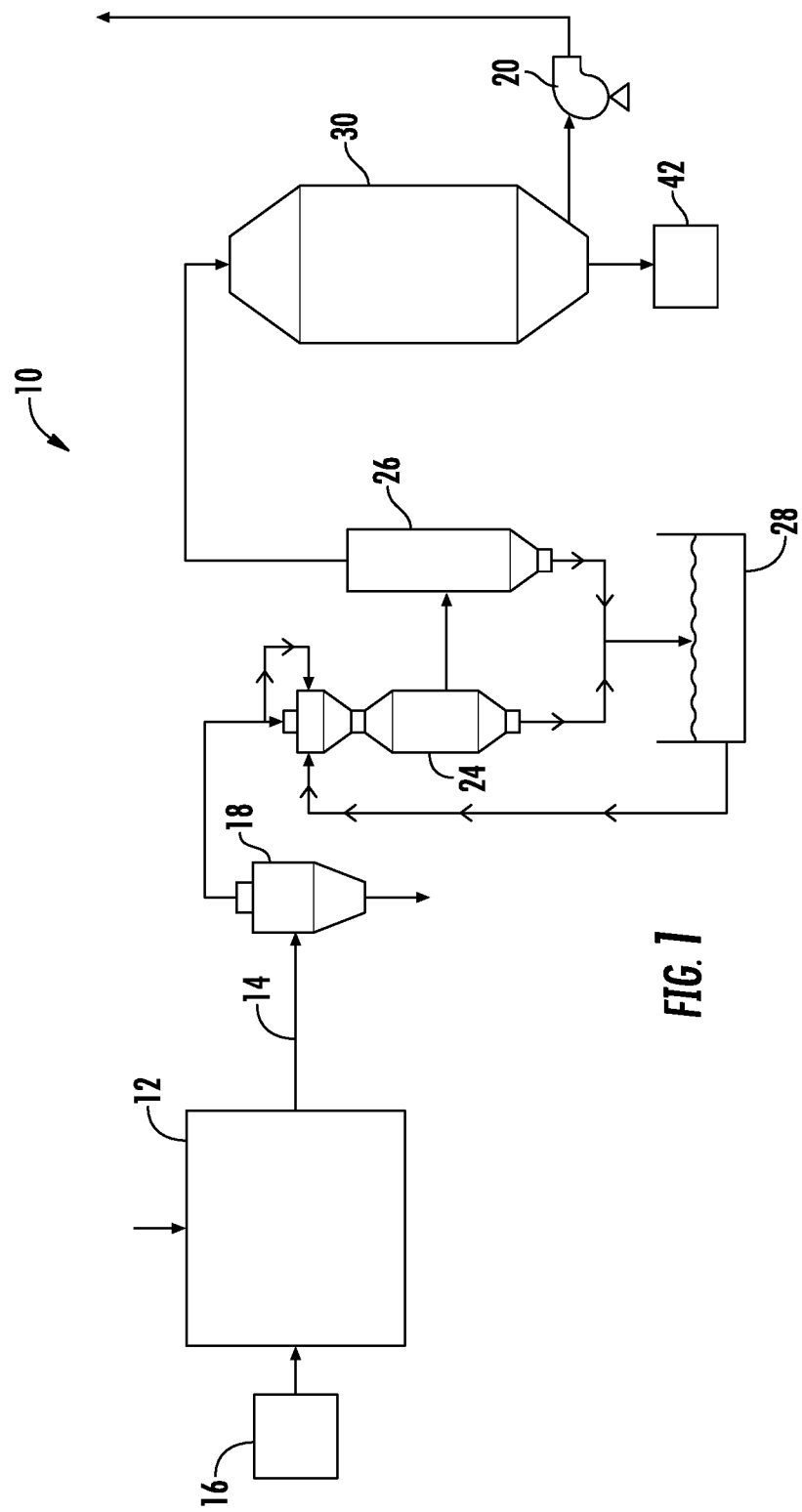
FIG. 1 is a schematic of a continuous biomass extraction system in accordance with the present disclosure.

The present disclosure relates to an extraction system 10, such as that shown in FIG. 1, for collecting a valuable organic extract from a biomass, such as hemp, herbs or hops, and a method for collecting a valuable organic extract from a biomass, such as hemp, herbs or hops. The extraction system 10 can include a biomass introduction unit 12 for providing the biomass to the system 10. The introduction unit 12 can include an auger for receiving and transporting ground biomass to a receiver, which is used to break up and direct the biomass toward a rotary seal connected to a first conduit 14 that connects a heat source 16 and a first separation unit 18. A gas, such as air or inert gas, is heated by the heat source 16 to be mixed with the biomass in the first conduit 14. The heated gas subjects the biomass to flash extraction and causes an enriched organic vapor to be created, thus vaporization of a portion of the biomass occurs in the first conduit 14.

A blower 20 can be attached to the tail end of the system 10 to provide a sufficient vacuum draw to the system 10 to keep the system 10 under negative pressure, thus allowing the biomass and resulting vapors to be pulled towards the end of the system 10. Alternatively, a blower 20 could be attached to the front end of the system 10 to create a positive pressure environment and push biomass and vapors through the system 10. In either embodiment, the air or inert gas flows through the heat source 16 where it reaches the process temperature, which is between 150° C. and 400° C. and can proceed into the first conduit 14 where the vaporization occurs. As the ground biomass is swept through the first conduit 14, the compounds of interest are vaporized into the airstream to form a dilute mixture of air/inert gas. The mixture of air/inert gas, oil vapors, and depleted biomass exit the first conduit 14 and are passed into the first separation unit 18, such as a cyclone separator that is used to separate the solid biomass from the enriched organic vapor. It should be understood and appreciated that the first separation unit 18 can be any apparatus known in the art capable of separating a solid (spent biomass) and gas (mixture of organic vapor and air/inert gas).

The portion of the first conduit 14 between where the heated gas and the biomass are combined and the first separation unit 18 can be sized (length and diameter) such that a requisite amount of enriched organic vapor is produced. Furthermore, the flowrate and temperature of the heated gas and the biomass in the first conduit 14 can be adjusted to make sure the requisite amount of enriched organic vapor is produced. The first conduit 14 can include multiple sections where the diameter is increased and/or decreased to create turbulent flow of the heated gas and the biomass as they are passed through the first conduit 14 and to the first separation unit 14.

The heated gas must be hot enough to allow the vapor pressure to become high enough that the enriched organic vapor will be suspended in the heated gas flowing through the first conduit 14. In one embodiment, the biomass and gas are heated to a temperature between about 100° C. and about 400° C. In another embodiment, the biomass and gas are heated to a temperature between about 175° C. and about 325° C. In a further embodiment of the present disclosure, the biomass and gas are heated to a temperature between about 165° C. and about 275° C.

The enriched organic vapor is separated from the biomass in the first separation unit 18 to create a biomass waste, which can be taken and sold or used to produce various other products. The first separation unit 18 can be any device capable of separating a solid material from a gaseous material. In one embodiment, the first separation unit 18 can be a cyclone that spins and forces the solid material outward in the cyclone and the gaseous material can generally be pulled from the top of the cyclone.

The enriched organic vapor, which contains water, air, terpenes, flavonoids, alkaloids, fatty acids, etc., is then sent to a wet scrubber 24 where the enriched organic vapor can be cooled to the natural adiabatic wet bulb temperature of the gas stream. In another example, the water in the wet scrubber 24 may be cooled to between 4° C. and 25° C. When the enriched organic vapor is cooled, the water vapor, terpenes and other vapor phase compounds disposed therein condense into liquid droplets. Some of these small droplets may be captured in the water used in the wet scrubber 24. The small droplets captured in the water of the wet scrubber 24 can be recycled back to the system 10, sent to a water bath 28 or separated into separate compounds and used for other purposes. The remaining particles of the enriched organic vapor, referred to as an organic smoke, will be pulled or pushed into a second separation unit 26 where entrained liquid droplets from the wet scrubber 24 and any dust particles still present are removed. Some of the organic liquid particles that may still be present are also removed in the second separation unit 26. This mixture of water droplets from the wet scrubber 24 plus some portion of the still present organic liquid particles are collected and sent to the water bath 28. In one embodiment, the second separation unit 26 is a cyclonic mist separator that spins the liquid entering and forces the liquid to the outer walls and permits the organic smoke, or cannabinoid particles if the biomass is hemp or *cannabis*, to pass to an electrostatic precipitator 30.

The organic smoke that leaves the second separation unit 26 and enters the electrostatic precipitator 30 are in the form of sub-micron droplets like a smoke or a fog. Water droplets that have escaped from the second separation unit 26 will be entrained with the organic smoke. These ultra-fine particles and fine water droplets need to be removed to be able to provide an organic oil. The electrostatic precipitator 30 can be any type of electrostatic precipitator known to one of ordinary skill in the art.

In one embodiment, the electrostatic precipitator 30 includes a tube 32 or array of tubes 32 disposed in a parallel arrangement. The tubes 32 may be round, square or hexagonal. Each tube 32 includes a discharge electrode 34 that is centrally located within each tube 32. The centrally located discharge electrode 34 is energized with unipolar high voltage to establish a strong electric field in the inner-electrode spacing between the discharge electrode 34 and an inner surface 36 of the tube 32 which must be electrically connect to ground. The electric field thus established must be strong enough to establish a stable corona discharge between the centrally located discharge electrode 34 and the inner surface 36 of the tube 32. The electrostatic precipitator also includes an inlet 38 for feeding the ultra-fine particles and fine water droplets to the electrostatic precipitator. The electrostatic precipitator 30 can also include an exhaust for expelling any vapor present in the electrostatic precipitator 30 from the electrostatic precipitator 30.

When the organic smoke and the entrained water droplets flow into the electric field the organic smoke particles and droplets become charged when they pass by the high voltage corona and are driven by the electric field to the inner surface 36 the tube 32. This organic liquid (or organic oil) will then drain by gravity into the bottom of the electrostatic precipitator 30 and be directed toward and outlet 39 where the organic oil can be captured.

The voltage of the electrodes needs to be high to accomplish the stated goal. The voltage can be between 10,000 volts to about 50,000 volts. In one embodiment, the discharge electrode can be negatively charged. In another embodiment, the discharge electrode can be positively charged.

The gas stream containing the organic smoke flowing through the inter-electrode zone of the electrostatic precipitator 30 can vary in velocity. In one embodiment, the velocity of the gas stream through the electrostatic precipitator 30 is low enough so that the flow of the gas stream is laminar in nature. Laminar flow occurs when the Reynolds number is less than 2000. In other embodiments the velocity of the gas stream flowing through the inner-electrode zone may be turbulent with a Reynolds number greater than 2000.

Figure 2:
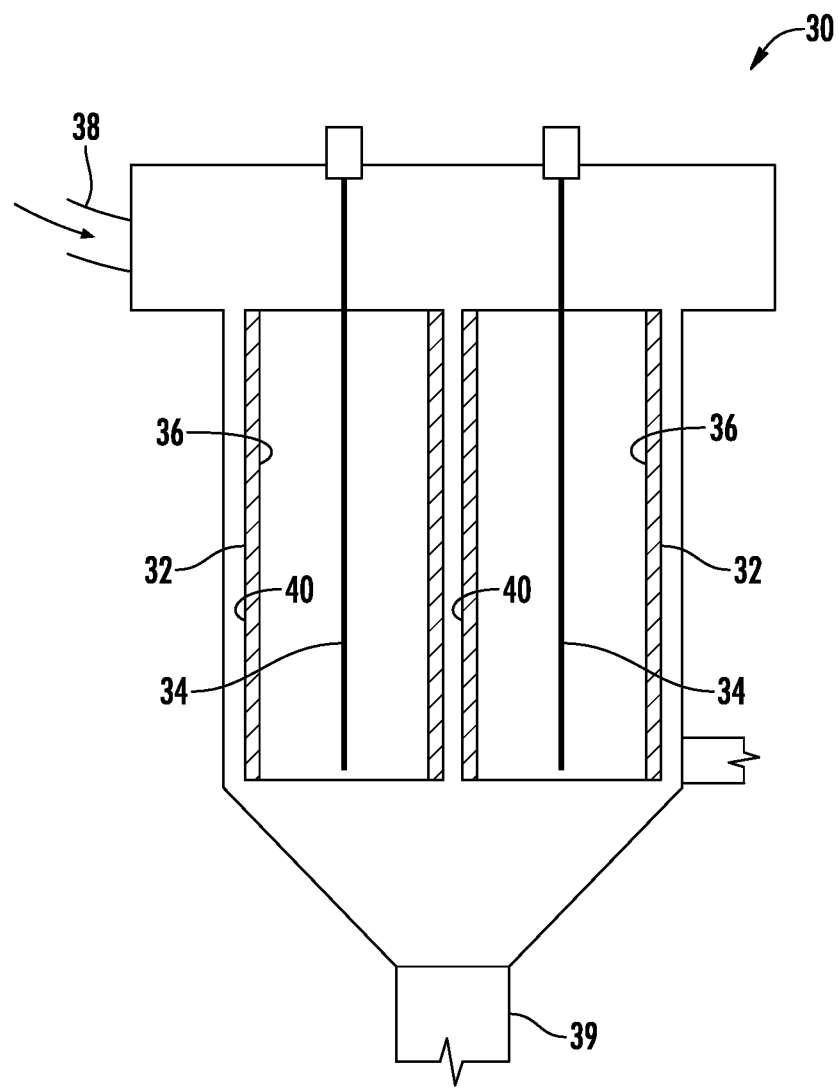
FIG. 2 is one embodiment of an electrostatic precipitator incorporated in the biomass extraction system in accordance with the present disclosure.

In another embodiment of the present disclosure shown in more detail in FIG. 2, the electrostatic precipitator 30 utilizes round tubes 32. The tubes 32 may be heated on an exterior surface 40 of the tubes 32 to encourage the flow of collected organic liquids on the inner surface 36 of the tube 32. The source of the heat may include a heated liquid such as hot water, thermal oil, pre-heated air or even electric resistance surface heaters.

In yet another embodiment, the organic oil will flow from the inner surfaces 36 of the tubes down into the water bath 28, wherein the organic oil will separate from and drop to the bottom of the water bath 28. In another embodiment, the organic oil exiting the electrostatic precipitator 30 can be sent to a separate collection vessel 42 from the water bath 30 that collected the condensate from the organic enriched vapor in previous steps. Similar to how the organic oil is recovered from the water bath 28, the organic oil can be removed from the bottom of the aqueous portion of the fluid in the separate collection vessel 42 dedicated to the fluid collected from the electrostatic precipitator 30.

In another embodiment of the present disclosure, the fluid in the water bath 30 can be recycled to the scrubber 24 to try and produce additional organic oil to be sent to the second separation unit 26.

Figure 3:
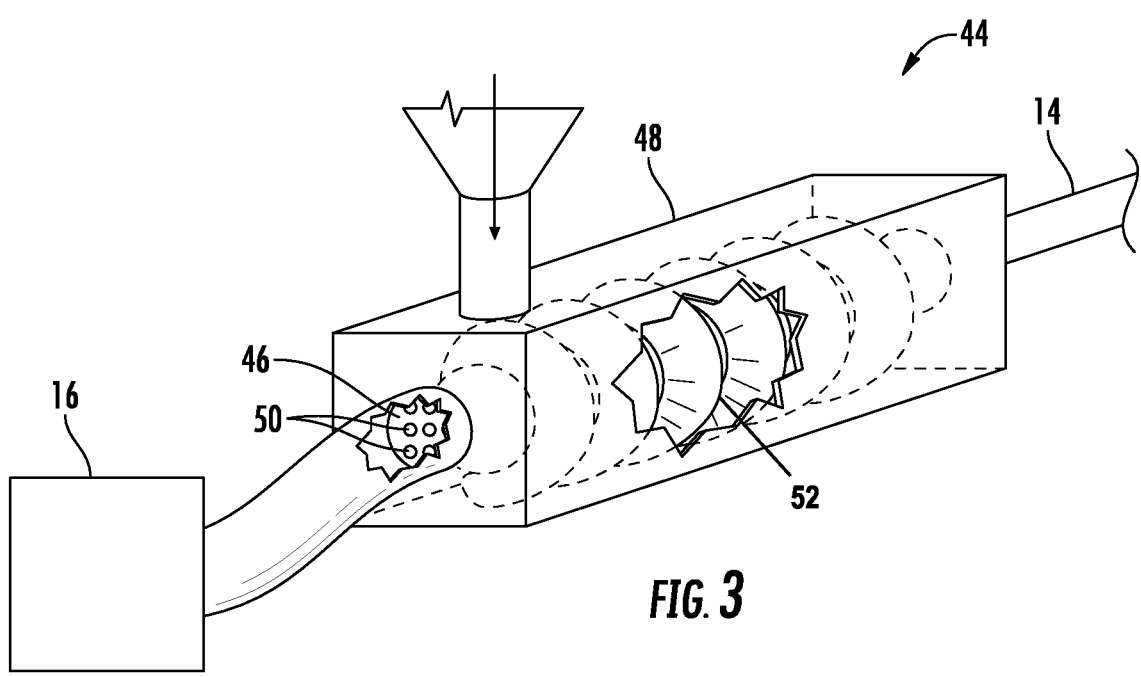
FIG. 3 is an auger apparatus incorporated in the biomass extraction system in accordance with the present disclosure.

In yet another embodiment of the present disclosure shown in more detail in FIG. 3, the biomass introduction unit 12 can direct the biomass to an auger apparatus 44. The auger apparatus 44 that can have a perforated portion 46 wherein at least a portion of the auger apparatus 44 is porous or perforated to permit the heated gas to flow directly into and through the auger apparatus 44 to heat the biomass in an auger chamber 48 of the auger apparatus 44. The porous portion 46 can be any structural portion of the auger apparatus 44 such as the walls, the top portion or the bottom portion. The porous portion 46 has openings 50 therein that are sized to permit the heated gas to flow through but would prevent the biomass from passing through. The flow rate of the heated gas through the openings 50 in the porous portion 46 would also contribute to preventing the biomass from passing through. The auger apparatus 44 would also include an auger 52 for driving the biomass through and out of the auger apparatus 44. In this embodiment, the auger apparatus 44 is in fluid communication with the heat source 16 and the heated gas flows from the heat source 16 to and through the auger apparatus 44. The solid biomass and generated enriched organic vapor then flow into the first conduit 14 that carries the biomass and the enriched organic vapor (cannabinoid enriched vapor in certain embodiments) to the first separation unit 18.

In a further embodiment of the disclosure, a fluidized bed contactor may be used to heat the biomass. Heated air is passed through a fine screen disposed on a bottom portion of the fluidized bed which allows the heated air to pass upward through the fine screen and tumble the ground biomass. The enriched organic vapors created from heating the biomass on the fluidized bed contactor can then be passed to the first separation unit 18 of the system 10.

The system and method described herein can yield certain results with respect to the compounds of value in the biomass. In an exemplary embodiment of the present disclosure, where the compound of value is cannabidiol (CBD) and the biomass is hemp and/or *cannabis*, a certain amount of the CBD can be recovered at various stages in the method and system. The amount of CBD in the biomass can be determined prior to passing into the system described herein. In one embodiment, the weight percent of CBD recovered after the biomass and the heated gas has been mixed and separated is greater than 40 percent. In another embodiment, the weight percent of CBD recovered after the biomass and the heated gas has been mixed and separated is greater than 65 percent. In a further embodiment, the weight percent of CBD recovered after the biomass and the heated gas has been mixed and separated is greater than 75 percent.

Further to the exemplary embodiment herein, the resulting valuable organic oil produced by the described system and method is primarily CBD oil and the system and method disclosed herein can produce a primarily CBD oil and has a certain potency. The CBD potency of the organic oil is the weight percent that CBD is of the total weight of the organic oil. In one embodiment, the CBD weight percent of the weight of the organic oil produced is greater than 70 percent. In another embodiment, the CBD weight percent of the weight of the organic oil produced is greater than 80 percent.

The amount of CBD in the biomass introduced to the system can be compared to the amount of CBD in the organic oil captured by the system. In one embodiment, the weight percent of CBD captured in the organic oil is greater than 30 percent of the total weight of the CBD in the biomass prior to being introduced to the system. In another embodiment, the weight percent of CBD captured in the organic oil is greater than 40 percent of the total weight of the CBD in the biomass prior to being introduced to the system.

Furthermore, the amount of CBD in the enriched organic vapor (the vapor created by mixing the heated gas and the biomass) can be evaluated versus the amount of CBD in the organic oil produced by the system. In one embodiment, the weight percent of the CBD contained in the organic oil is greater than 40 percent of the weight of the CBD contained in the enriched organic vapor entering the first separation unit or exiting the first separation unit. In another embodiment, the weight percent of the CBD contained in the organic oil is greater than 50 percent of the weight of the CBD contained in enriched organic vapor entering the first separation unit or exiting the first separation unit.

From the above description, it is clear that the present disclosure is well-adapted to carry out the objectives and to attain the advantages mentioned herein, as well as those inherent in the disclosure. While presently preferred embodiments have been described herein, it will be understood that numerous changes may be made which will readily suggest themselves to those skilled in the art and which are accomplished within the spirit of the disclosure and claims.

What is claimed is:

1. A method for producing organic liquid from a biomass, the method comprising:
   mixing a biomass with a heated gas to produce an enriched organic vapor and a biomass waste product;
   separating the enriched organic vapor from the biomass waste product;
   cooling the enriched organic vapor in a wet scrubber to remove certain compounds from the enriched organic vapor to produce an enriched organic smoke;
   separating entrained liquid droplets and biomass dust particles exiting the wet scrubber from the enriched organic smoke via a cyclonic mist separator;
   transforming the enriched organic smoke to a liquid organic oil; and
   collecting the liquid organic oil.

2. The method of claim 1, further comprising a step of depositing the biomass into a conduit where the biomass is mixed with the heated gas.

3. The method of claim 1, wherein the liquid organic oil is generated from the enriched organic vapor with an electrostatic precipitator.

4. The method of claim 3, where the electrostatic precipitator is operated with positive or negative polarity.

5. The method of claim 3, where the electrostatic precipitator is operated within a laminar flow regime within an inner electrode zone.

6. The method of claim 3, where the electrostatic precipitator includes parallel collecting tubes wherein each collecting tube has an inner surface and an exterior surface.

7. The method of claim 6, where the parallel collecting tubes are heated to facilitate the downward flow of the liquid organic oil down the inner surfaces of the tubes of the electrostatic precipitator.

8. The method of claim 1, wherein the biomass is hemp or *cannabis* and the liquid organic oil is primarily comprised of cannabidiol (CBD) oil and the weight percent of the CBD oil is greater than 70 percent of the weight of the liquid organic oil.

9. The method of claim 1, wherein all steps are conducted at atmospheric pressure.

10. The method of claim 1 wherein all steps are conducted free of the use of any solvents.

11. A system for producing organic liquid from a biomass, the system comprising:
    a first cyclonic separation unit to separate an enriched organic vapor and a biomass waste product, the enriched organic vapor and biomass waste product generated from mixing a heated gas and a biomass;
    a wet scrubber for cooling the enriched organic vapor to remove certain compounds from the enriched organic vapor to generate an enriched organic smoke;
    a cyclonic mist separator to separate entrained liquid droplets and biomass dust particles exiting the wet scrubber from the enriched organic smoke; and
    an electrostatic precipitator for transforming the enriched organic smoke to a liquid organic oil.

12. The system of claim 11, where the electrostatic precipitator includes parallel collecting tubes wherein each collecting tube has an inner surface and an exterior surface.

13. The system of claim 12, where the enriched organic smoke entering the electrostatic precipitator flows downwardly through the tubes.

14. The system of claim 13, where the parallel collecting tubes are heated to facilitate the flow of the liquid organic oil down the inner surfaces of the tubes of the electrostatic precipitator.

15. The system of claim 11, wherein all components of the system operate at atmospheric pressure.

16. The system of claim 11, wherein all components of the system operate free of the use of any solvents.

17. The system of claim 11, wherein the biomass can continually be fed to the system and the liquid organic oil can continuously be produced.

18. The system of claim 11, further comprising a conduit disposed between a heat source that produces the heated gas and the first cyclonic separation unit where the biomass and the heated gas can be mixed.

* * * * *